United States Patent
Friedman et al.

[11] Patent Number: 5,942,244
[45] Date of Patent: Aug. 24, 1999

[54] LOCAL ORAL HERBAL SLOW RELEASE TABLETS

[75] Inventors: Michael Friedman, Jerusalem; Orna Levin, Kfar-Neter; Yochanan Forman, Kibbutz Maabarot; Doron Friedman, Karme-Yosef, all of Israel

[73] Assignee: Farmo-Nat Ltd., Ashkelon, Israel

[21] Appl. No.: 08/904,248

[22] Filed: Jul. 31, 1997

[51] Int. Cl.$^6$ ................................ A61K 9/22; A61K 9/26
[52] U.S. Cl. ..................... 424/435; 424/464; 424/465; 424/468; 424/469; 424/484; 424/486; 424/488; 514/770; 514/772.3; 514/777; 514/781; 514/960; 514/965
[58] Field of Search ...................... 424/464, 465, 424/435, 484, 468, 469, 488, 486; 514/960, 965

[56] References Cited

U.S. PATENT DOCUMENTS 4,292,299  9/1981  Suzuki et al. ........................ 424/435

*Primary Examiner*—Thurman K. Page
*Assistant Examiner*—James M. Spear
*Attorney, Agent, or Firm*—Mark M. Friedman

[57] ABSTRACT

A tablet for the local and slow release of herbal medication into the oral cavity of a subject. Also provided is a method of making the tablet and a method of using the tablet. The tablet includes a pharmaceutically effective amount of a herbal medication, a polymeric matrix material such as ethyl cellulose, a release enhancer such as PEG 4000 and a filler such as lactose. The tablet is characterized by long dissolution times of up to 120 minutes.

26 Claims, 2 Drawing Sheets

Release rates from tablets

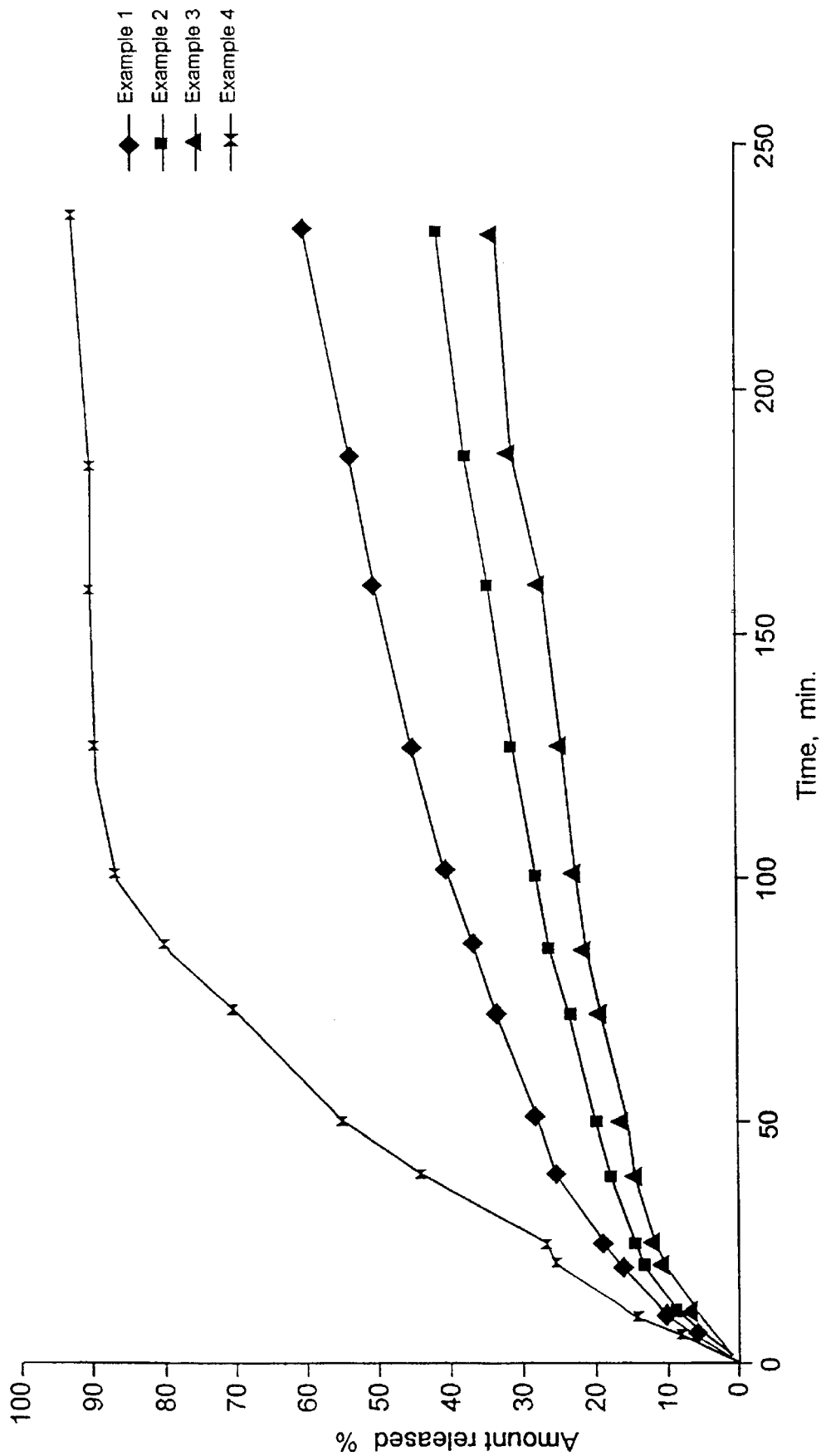
Fig. 1 Release rates from tablets

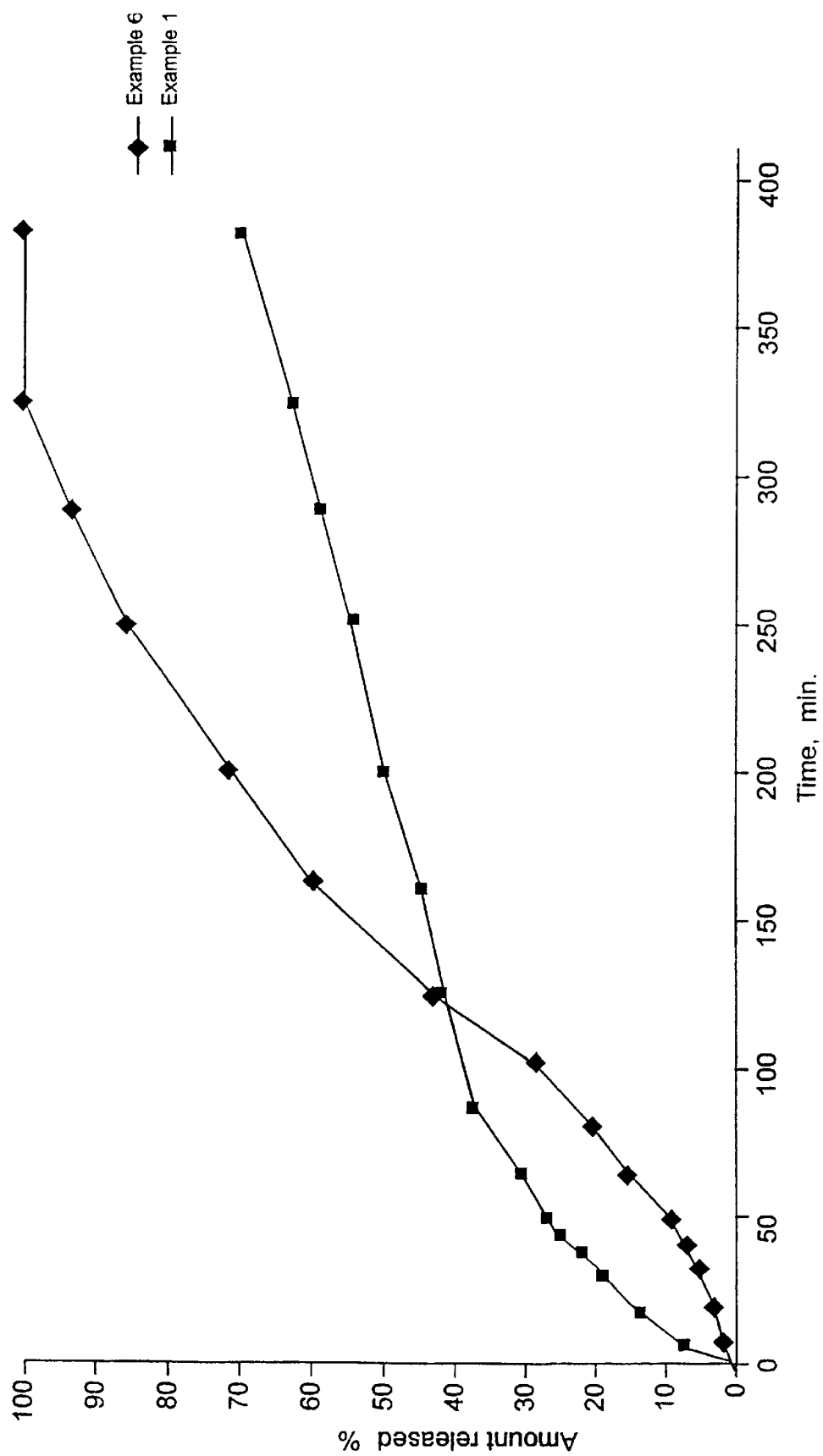
Fig. 2 Comparison of example 1 and 6

LOCAL ORAL HERBAL SLOW RELEASE TABLETS

FIELD AND BACKGROUND OF THE INVENTION

The present invention relates to slow release tablets for oral administration and, more particularly, to tablets which permit a prolonged period of contact between the medication and the buccal and gingival mucosa as well as the hard and soft tissues of the mouth.

Medications are generally administered with a pharmaceutical carrier with specific desired characteristics which can, for example, influence the rate of release of the medication from the carrier. The choice of carrier is thus determined by the desired medical outcome. For example, medications which have local effects in the mouth and throat are often administered in both solid and liquid form, depending upon the desired pharmaceutical effect.

Liquid and semi-liquid dosage forms, such as mouthwashes and toothpastes are frequently used for oral hygiene, but have the disadvantage of relatively short contact periods with the hard and soft tissues of the mouth and throat. Solid dosage forms, such as troches and lozenges, offer certain advantages for such local administration of oral medications. The terms lozenge and troche are used synonymously for any form of tablet designed to be held in the mouth for slow dissolution and release of medication such that prolonged contact of the medication with the mouth and throat is ensured. The medications administered with troches or lozenges are primarily local anesthetics, antiseptics, astringents or anti-tussives. Lozenges may be made by fusion, a candy molding process or by compression. Troches are usually manufactured by compression, as are most other tablets.

Although currently available troches and lozenges have the advantage of enabling medication to be in prolonged contact with the mouth and throat, such tablets still have a number of disadvantages. First, although troches and lozenges do not dissolve immediately, the rate of release of medication is still relatively rapid, on the order of about 15 minutes for total release. Second, these dosage forms have not been specifically tested with herbal medications, or medications derived from botanical materials. Thus, the efficacy of these dosage forms with herbal medications is unknown. Hereinafter, the term "herbal medication" refers to a medication derived from botanical materials or a biologically active extract of these materials.

There is thus a widely recognized need for, and it would be highly advantageous to have, a solid dosage form for oral administration of medication with local effects on the mouth and throat, which permits release of the medication over a prolonged period of time, which has been specifically tested for use with herbal medications and which permits prolonged contact between the active ingredient of the medication and the hard and soft tissues of the mouth and throat.

SUMMARY OF THE INVENTION

According to the present invention there is provided a tablet for prolonged release of a medication, including: (a) a pharmaceutically effective amount of a herbal medication as the medication; (b) a polymeric matrix material; (c) a release enhancer; and (d) a filler. Preferably, the polymeric matrix material is ethyl cellulose. More preferably, the ethyl cellulose is present in an amount of from about 11 percent to about 53 percent, weight per weight. Also preferably, the release enhancer is polyethylene glycol 4000. More preferably, the polyethylene glycol 4000 is present in an amount of from about 8 percent to about 28 percent weight per weight. Preferably, the filler is lactose. More preferably, the lactose is present in an amount of from about 9 percent to about 57 percent weight per weight. Preferably, the herbal medication includes a herbal extract and the tablet further includes fume silica as an absorbing agent for the herbal extract. Preferably, the tablet includes a flavoring agent, a coloring agent or both.

According to another embodiment of the present invention, there is provided a method of releasing a medication in an oral cavity of a subject, including the steps of: (a) placing a tablet in the oral cavity of the subject, the tablet including: (i) a pharmaceutically effective amount of a herbal medication as the medication; (ii) a polymeric matrix material; (iii) a release enhancer; and (iv) a filler; and (b) allowing the tablet to dissolve in the oral cavity of the subject, such that the medication is released.

Hereinafter, the term "subject" is the human to whom the tablet of the present invention is administered.

Hereinafter, the term "herbal medication" can include one or more herbal extracts, one or more essential oils, or a combination of both.

Herbal extracts are extracts of plant materials, such as a tincture of botanical materials, which are prepared by contacting botanical material with a solvent [*British Herbal Pharmacopeia*, Peter R. Bradley, ed., British Herbal Medicine Association, 1983; and *British Herbal Compendium*, Peter R. Bradley, ed., British Herbal Medicine Association, 1992]. The solvent can be aqueous or organic, or a combination thereof. Acceptable organic solvents include, but are not limited to, glycerin, propylene glycol or alcohol, or a combination thereof. The most preferred solvents are hydroalcoholic solvents as defined in *British Herbal Pharmacopeia and Compendium*. The botanical material can include, but is not limited to, one or more of the following species: Plantago (*Plantago major*), Hypericum (*Hypericaceae perforatus*), Echinacea (Coneflower) (Echinaceae species such as *Echinaceae angustifoliae radix* and *Echinaceae purpurea*), Baptisia, Calendula, Myrrh, Phytolaca, Salvia, Catechu black, Krameria, Tsuga, Rosmarinus, Styrax, Crataegus, Glycerrhiza (*Glycerrhiza glabra*), Angelica, Krameria, Matricaria, Mallow and Sage. Propolis is the resinous substance found in beehives. Although strictly speaking Propolis is not a botanical material, extracts of this material are prepared in a substantially similar manner as extracts of the plant materials and are hereinafter included in the term "herbal extract".

An essential oil is a volatile mixture of esters, aldehydes, alcohols, ketones and terpenes, which can be prepared from botanical materials or plant cell biomass from cell culture. Examples of essential oils include, but are not limited to, oil of cinnamon, prepared from the dried bark of the roots of *Cinnamomum zeyloriaceae*; cajeput oil, eucalyptus oil, prepared from the fresh leaves and branches of various species of Eucalyptus, such as *E. globulus*; fennel oil, prepared from dried ripe fruit of *Foeniculum vulgare*; geranium oil, prepared from the aerial parts of Pelargonium species; girofle oil, lavander oil, prepared from fresh flowering tops of Lavandula species such as *Lavandula officinalis*; lemon oil, obtained from the fresh peel of Citrus limon; spearmint oil, prepared from the overground parts of fresh flowering Mentha species, such as *M. spicata*; myrte oil, origano oil, pine oil, rosemary oil, prepared from tops or leafy twigs of *Rosmarinus officinalis*; sarriette oil, thyme oil, prepared from the leaves and flowering tops of *Thymus vulgaris*; and tea-tree oil, obtained from the leaves of *Melaleuca olternifolia*.

BRIEF DESCRIPTION OF THE DRAWINGS

Results of tests performed on tablets of the invention are herein described, by way of example only, with reference to the accompanying drawings, wherein:

FIG. 1 is a graph of the rate of release of the medication contained in the tablets of the present invention of the formulas in Examples 1–4; and FIG. 2 is a further graph of the rate of release of the medication contained in another embodiment of the tablets of the present invention as shown by a comparison of the tablets of Example 5 and Example 1.

DESCRIPTION OF THE PREFERRED EMBODIMENTS

The present invention is of a solid oral dosage form which enables the slow release of medication in the oral cavity. Specifically, the solid oral dosage form of the present invention enables a prolonged period of contact of the released medication with the mouth and throat, either by slow dissolution or disintegration of the solid dosage form. Furthermore, the solid dosage form is specifically designed to be used with herbal medications.

Although the following description will refer to the solid dosage form as a "tablet" for the sake of clarity, it should be understood that the present invention is not restricted to any one type of tablet, but could also be in the form of troches or lozenges, for example.

Formulations of Slow Release Tablets

The slow release tablets of the present invention include the following ingredients: the herbal medication itself, a polymeric matrix material, a release enhancer and a filler.

The choice of a particular polymeric matrix material, as well as the amount which is used, has a strong influence on the rate of release of medication from the tablets of the present invention. Examples of polymers for matrix formation include both hydrophobic and hydrophilic polymers. Examples of hydrophobic polymers include, but are not limited to, ethyl cellulose and other cellulose derivatives, fats such as glycerol palmito-stereat, beeswax, glycowax, castorwax, carnaubawax, glycerol monostereate or stearyl alcohol, hydrophobic polyacrylamide derivatives and hydrophobic methacrylic acid derivatives, as well as mixtures of these polymers. Hydrophilic polymers include, but are not limited to, hydrophilic cellulose derivatives such as methyl cellulose, hydroxypropylmethyl cellulose, hydroxyethylcellulose, hydroxypropyl cellulose, carboxymethyl cellulose, sodium carboxymethylcellulose and hydroxyethyl methylcellulose, as well as mixtures of these polymers. Furthermore, any mixture of one or more hydrophobic polymer and one or more hydrophilic polymer could optionally be used.

Ethyl cellulose is particularly preferred as the polymeric matrix material for the tablets of the present invention, and is preferably present in an amount of from about 11 to about 53 percent, weight per weight.

Examples of release enhancers which modify the rate at which medication is released from the polymeric matrix material include, but are not limited to, glycerol and polyethylene glycols (PEG) of different molecular weights, e.g. PEG 300, PEG 400, PEG 1000, PEG 4000, PEG 6000, PEG 10,000 and others. PEG 4000 is the preferred release enhancer because it causes the polymeric matrix material to dissolve slowly in aqueous solutions. PEG 4000 is preferably present in an amount of from about 8 to about 28 percent, weight per weight.

Examples of pharmaceutically acceptable fillers include lactose, sucrose, mannitol and others. Lactose is the preferred filler and is preferably present in an amount of from about 9 to about 57 percent, weight per weight. Optional ingredients include coloring and flavoring agents which are well known in the art.

Preparation of the tablets of the present invention requires the addition of a wetting agent at one point in the procedure. The wetting agent is preferably a solution of water and alcohol. However, it should be noted that one ingredient in the tablets of the present invention can be a herbal extract, which is itself a liquid. The addition of the herbal extract to the tablet presents a challenge, since large amounts of liquid are not well incorporated into tablets, which are dry solids. This problem is solved in one of two ways.

The first solution is simply to use the herbal extract itself as the wetting agent. Since, as noted previously, herbal extracts are prepared by contacting botanical materials with a solvent which is preferably a mixture of alcohol and water, the herbal extract contains the same liquid ingredients as the wetting agent. Therefore, the herbal extract is an ideal replacement for the standard wetting agent.

However, in some instances, it is desirable to add such large quantities of herbal extract that even substituting the extract for the wetting agent is not sufficient. This problem is solved by first absorbing some or all of the herbal extract onto fume silica, which is an absorbing agent with a large absorbent surface area. The combination of the extract and the fume silica can be added is to the tablet without destroying the integrity of the tablet itself. Fume silica is commercially available from Rhone-Poulenc, France as "Tixosil", for example.

A number of examples of tablets of the present invention are given below for purposes of illustration only and are not intended to be limiting. Furthermore, for the purposes of evaluation only and unless otherwise detailed, the herbal medication used in the methods detailed below was natural xantines from freeze-dried ripe seeds of *Coffea rubiaceae*, added in the form of coarsely ground powder, hereinafter referred to as "coffee powder", and an essential oil. The essential oil used was Eucalypti oil, Cinnamon oil or Tea tree oil, although other oils could also be used, alone or in combination.

The tablets of the present invention were evaluated by using the following methods. Two separate tests were performed, a dissolution and release test in a standard rotating basket assembly, and a release test in the oral cavity of a subject.

The dissolution test was performed in accordance with the USP (United States Pharmacopeia). The speed of rotation of the basket was 150 revolutions per minute. The dissolution medium was 0.9% NaCl solution in purified water. The basket was a cylindrical vessel with a flat bottom capable of holding 1000 ml of dissolution medium. For the release test in the standard assembly, results are presented as the percentage of herbal medication released over time.

For the release test in the oral cavity, five separate tests were performed on five separate human subjects. Each subject held the tablet in the mouth and timed how long the tablet took to completely dissolve or disintegrate. Thus, this was an in vivo test of the performance of the tablets of the present invention. Furthermore, this test is identical to the actual method of use of the tablets of the present invention.

The formulation and method of production of each tablet is given below as a separate, illustrative example.

EXAMPLE 1

The tablet of Example 1 had the following ingredients, as given in the table below.

| Tablet Ingredients | Amount (% weight per weight) |
|---|---|
| Ethyl Cellulose | 20.0 |
| PEG 4000 | 25.0 |
| Lactose | 25.0 |
| Coffee Powder | 28.0 |
| Eucalypti oil | 2.0 |

The method of preparation of this tablet formulation was as follows. A thick dough was obtained by massing about 5 g of PEG 4000 with about 6.0 ml of ethanol (absolute). A powdered mixture of about 5 g of lactose and 5.6 g of coffee powder was added to the thick dough. About 1.5 ml of ethanol was then added to finish the massing of the dough. The dough was then pressed through a 1.6 mm screen of an Eureka granulation machine to form a granulation. The granulation was dried in an oven at about 53° C. for 1.5 hours.

After cooling, the mixture was ground with a hand-held mortar and pestle. Eucalypti oil was added to the ground mixture by dispersion to form the final granulation. This granulation was then compressed into tablets in a tablet press. The tablet compression was about 10 Torr, for a tablet of about 1 g weight, 10 mm diameter and 4 mm thickness.

The tablet was tested by using the diand release tests described below. After 65 minutes in the dissolution test, the percentage of herbal medication released was 32%. During the oral release test, the tablet completely dissolved after about 45–50 minutes.

EXAMPLE 2

The tablet of Example 2 had the following ingredients, as given in the table below.

| Tablet Ingredients | Amount (% weight per weight) |
|---|---|
| Ethyl Cellulose | 30.0 |
| PEG 4000 | 20.0 |
| Lactose | 20.0 |
| Coffee Powder | 28.0 |
| Eucalypti oil | 2.0 |

The tablets were prepared as for Example 1 above, except that the proportions of the ingredients were changed. After 65 minutes, the percentage of herbal medication released was about 24.7%. The tablets required about 65–70 minutes in the oral cavity to completly dissolve.

EXAMPLE 3

The tablet of Example 3 had the following ingredients, as given in the table below.

| Tablet Ingredients | Amount (% weight per weight) |
|---|---|
| Ethyl Cellulose | 50.0 |
| PEG 4000 | 10.0 |
| Lactose | 10.0 |
| Coffee Powder | 28.0 |
| Eucalypti oil | 2.0 |

The tablets were prepared as for Example 1 above, except that the proportions of the ingredients were changed. After 65 minutes, the percentage of herbal medication released was about 18.6%. The tablets required about 120 minutes in the oral cavity to completly dissolve.

EXAMPLE 4

The tablet of Example 4 had the following ingredients, as given in the table below.

| Tablet Ingredients | Amount (% weight per weight) |
|---|---|
| Ethyl Cellulose | 11.5 |
| PEG 4000 | 8.0 |
| Lactose | 54.5 |
| Coffee Powder | 24.0 |
| Eucalypti oil | 2.0 |

The tablets were prepared as for Example 1 above, except that the proportions of the ingredients were changed. After 65 minutes, the release profile was about 68.6%. The tablets required about 10–15 minutes in the oral cavity to completly dissolve.

The results of the tests performed in the standard rotating basket assembly for the tablets of Examples 1–4 are given in FIG. 1. FIG. 1 shows the results of the release test, with the release profile given as a percentage over time. The diamonds indicate results obtained for the tablet of Example 1. Similarly, squares indicate tablets of Example 2, triangles tablets of Example 3 and crosses tablets of Example 4. Clearly, tablets of Example 4 dissolved the most quickly and tablets of Example 3 dissolved the most slowly.

Table 1 shows the results for the oral release test, conducted on the tablets of Examples 1–4. Again, tablets of Example 4 released the herbal medication the most quickly, and those of Example 3 released the medication the most slowly. Thus, the results of the in vitro and in vivo tests match in terms of the relative table dissolution rates.

TABLE 1

Results of Oral Release Test

| Formula | Time for Complete Tablet Disintegration In Vivo |
|---|---|
| Example 4 | 10–15 minutes |
| Example 1 | 45–50 minutes |
| Example 2 | 65–70 minutes |
| Example 3 | 120 minutes |

EXAMPLE 5

The tablet of Example 5 had the following ingredients, as given in the table below.

| Tablet Ingredients | Amount (% weight per weight) |
|---|---|
| Ethyl Cellulose | 20.0 |
| PEG 4000 | 25.0 |
| Lactose | 15.0 |
| Propolis Powder | 15.0 |
| Myrrh Powder | 15.0 |
| Cinnamon oil | 2.0 |

The tablets were prepared as for Example 1 above, except that the herbal medication was a combination of Myrrh and Propolis powders, and of Cinnamon oil, rather than ground coffee and Eucalypti oil. The results of a comparison of the release rate to tablets of Example 1 is given in FIG. 2. As can be seen from FIG. 2, tablets of Example 5 dissolved much more slowly than tablets of Example 1.

Other Formulas for Slow Release Tablets

Other examples of suitable formulas for slow release tablets according to the present invention are given below.

EXAMPLE 6

| Tablet Ingredients | Amount (% weight per weight) |
| --- | --- |
| Ethyl Cellulose | 15.7 |
| PEG 4000 | 19.6 |
| Lactose | 27.5 |
| Myrrh | 5.0 |
| Propolis | 10.73 |
| Plantago | 0.21 |
| Hypericum | 0.27 |
| Coneflower | 0.20 |
| Menthe oil | 5.0 |
| Tixosil 43 | 15.6 |
| Sodium saccharin | 0.19 |

It should be noted that three of the ingredients, Plantago, Hypericum and Coneflower, are liquid extracts (tinctures) which are present in a total amount of 39% volume per total weight of the tablet.

Tablets of Example 6 were prepared as follows. First, the liquid extracts were mixed together. Next, sodium saccharin was mixed with the liquid extracts. This mixture was added to powdered PEG 4000 to form a second mixture. An ethyl cellulose mixture was prepared by mixing ethyl cellulose with 3.5 ml of ethanol. The second mixture and the ethyl cellulose mixture were then mixed well in a mortar. Lactose, Myrrh and Propolis were then added to the mixture in the mortar to form a dough. Tixosil 43 (fume silica) was then added to the dough to form the final dough. The final dough was then pressed through a 1.6 mm screen of an Eureka granulation machine to form a granulation. The granulation was dried in an oven at about 53° C. for 1.5 hours.

After cooling, the mixture was ground with a hand-held mortar and pestle. Menthe oil was added to the ground mixture by dispersion to form the final granulation. This granulation was then compressed into tablets in a tablet press. The tablet compression was about 10 Torr, for a tablet of about 1 g weight, 10 mm diameter and 4 mm thickness.

EXAMPLE 7

| Tablet Ingredients | Amount (% weight per weight) |
| --- | --- |
| Ethyl Cellulose | 15.7 |
| PEG 4000 | 19.6 |
| Lactose | 27.5 |
| Myrrh | 5.0 |
| Propolis | 10.73 |
| Plantago | 0.21 |
| Hypericum | 0.27 |
| Coneflower | 0.20 |
| Menthe oil | 2.5 |
| Thyme oil | 2.5 |
| Tixosil 43 | 15.6 |
| Sodium saccharin | 0.19 |

It should be noted that as in Example 6, three of the ingredients, Plantago, Hypericum and Coneflower, are liquid extracts (tinctures).

Tablets of Example 7 were prepared as for tablets of Example 6, except that both Menthe oil and Thyme oil were added to the ground mixture by dispersion to form the final granulation.

EXAMPLE 8

| Tablet Ingredients | Amount (% weight per weight) |
| --- | --- |
| Ethyl Cellulose | 15.7 |
| PEG 4000 | 19.6 |
| Lactose | 27.5 |
| Myrrh | 5.0 |
| Propolis | 10.73 |
| Plantago | 0.21 |
| Hypericum | 0.27 |
| Coneflower | 0.20 |
| Menthe oil | 3.0 |
| Cinnamon oil | 2.0 |
| Tixosil 43 | 15.6 |
| Sodium saccharin | 0.19 |

It should be noted that as in Example 6, three of the ingredients, Plantago, Hypericum and Coneflower, are liquid extracts (tinctures).

Tablets of Example 8 were prepared as for tablets of Example 6, except that both Menthe oil and Cinnamon oil were added to the ground mixture by dispersion to form the final granulation.

EXAMPLE 9

| Tablet Ingredients | Amount (% weight per weight) |
| --- | --- |
| Ethyl Cellulose | 15.7 |
| PEG 4000 | 19.6 |
| Lactose | 27.5 |
| Myrrh | 1.0 |
| Propolis | 14.73 |
| Plantago | 0.21 |
| Hypericum | 0.27 |
| Coneflower | 0.20 |
| Menthe oil | 3.0 |
| Cinnamon oil | 2.0 |
| Tixosil 43 | 15.6 |
| Sodium saccharin | 0.19 |

It should be noted that as in Example 6, three of the ingredients, Plantago, Hypericum and Coneflower, are liquid extracts (tinctures).

Tablets of Example 9 were prepared as for tablets of Example 8.

EXAMPLE 10

| Tablet Ingredients | Amount (% weight per weight) |
| --- | --- |
| Ethyl Cellulose | 15.7 |
| PBG 4000 | 19.6 |
| Lactose | 27.5 |
| Myrrh | 1.0 |
| Propolis | 14.73 |
| Plantago | 0.21 |
| Hypericum | 0.27 |
| Coneflower | 0.20 |
| Thyme oil | 3.0 |
| Cinnamon oil | 2.0 |
| Tixosil 43 | 15.6 |
| Sodium saccharin | 0.19 |

It should be noted that as in Example 6, three of the ingredients, Plantago, Hypericum and Coneflower, are liquid extracts (tinctures).

Tablets of Example 10 were prepared as for tablets of Example 6, except that both Thyme oil and Cinnamon oil, instead of Menthe oil, were added to the ground mixture by dispersion to form the final granulation.

It will be appreciated that the above descriptions are intended only to serve as examples, and that many other embodiments are possible within the spirit and the scope of the present invention.

What is claimed is:

1. A tablet for prolonged release of a medication, comprising:
   (a) a pharmaceutically effective amount of a herbal medication as the active medication;
   (b) a polymeric matrix material;
   (c) a release enhancer; and
   (d) a filler;
   wherein said herbal medication, said polymeric matrix material, said release enhancer and said filler are present in a single layer.

2. The tablet of claim 1, wherein said polymeric matrix material is ethyl cellulose.

3. The tablet of claim 2, wherein said ethyl cellulose is present in an amount of from about 11 percent to about 53 percent, weight per weight.

4. The tablet of claim 1, wherein said release enhancer is polyethylene glycol 4000.

5. The tablet of claim 4, wherein said polyethylene glycol 4000 is present in an amount of from about 8 percent to about 28 percent weight per weight.

6. The tablet of claim 1, wherein said filler is lactose.

7. The tablet of claim 6, wherein said lactose is present in an amount of from about 9 percent to about 57 percent weight per weight.

8. The tablet of claim 1, wherein said herbal medication includes a herbal extract, the tablet further comprising fume silica as an absorbing agent for said herbal extract.

9. The tablet of claim 1, further comprising a coloring agent.

10. The tablet of claim 1, further comprising a flavoring agent.

11. A method of releasing a medication in an oral cavity of a subject, comprising the steps of:
    (a) placing a tablet in the oral cavity of the subject, the tablet including;
       (i) a pharmaceutically effective amount of a herbal medication as the active medication;
       (ii) a polymeric matrix material;
       (iii) a release enhancer; and
       (iv) a filler;
    wherein said herbal medication said polymeric matrix material, said release enhancer and said filler are present in a single layer; and
    (b) allowing said tablet to dissolve in the oral cavity of the subject, such that the medication is released.

12. The method of claim 11, wherein said polymeric matrix material is ethyl cellulose.

13. The method of claim 12, wherein said ethyl cellulose is present in an amount of from about 11 percent to about 53 percent, weight per weight.

14. The method of claim 11, wherein said release enhancer is polyethylene glycol 4000.

15. The method of claim 14, wherein said polyethylene glycol 4000 is present in an amount of from about 8 percent to about 28 percent weight per weight.

16. The method of claim 11, wherein said filler is lactose.

17. The method of claim 16, wherein said lactose is present in an amount of from about 9 percent to about 57 percent weight per weight.

18. The method of claim 11, wherein the herbal medication includes a herbal extract, said tablet further including fume silica as an absorbing agent for said herbal extract.

19. The method of claim 11, wherein said tablet further includes a coloring agent.

20. The method of claim 11, wherein said tablet further includes a flavoring agent.

21. A tablet for prolonged release of a medication, comprising:
    (a) a pharmaceutically effective amount of a herbal medication as the active medication;
    (b) a polymeric matrix material;
    (c) a release enhancer; and
    (d) a filler;
    wherein said herbal medication, said polymeric matrix material, said release enhancer and said filler are present in a single layer and wherein said single layer has a matrix structure.

22. A tablet for prolonged release of a medication, comprising:
    (a) a pharmaceutically effective amount of a herbal medication as the active medication;
    (b) a polymeric matrix material;
    (c) a release enhancer; and
    (d) a filler;
    wherein said herbal medication, said polymeric matrix material, said release enhancer and said filler are present in a single layer and wherein the tablet is a matrix tablet, thereby obviating the use of a disintegrator.

23. A tablet for prolonged release of a medication, consisting essentially of:
    (a) a pharmaceutically effective amount of a herbal medication as the active medication;
    (b) a polymeric matrix material;
    (c) a release enhancer; and
    (d) a filler;
    wherein said herbal medication includes a herbal extract, the tablet further comprising fume silica as an absorbing agent for said herbal extract.

24. A tablet for prolonged release of a medication, consisting essentially of:
    (a) a pharmaceutically effective amount of a herbal medication as the active medication;
    (b) a polymeric matrix material;
    (c) a release enhancer; and
    (d) a filler.

25. A tablet for prolonged release of a medication, consisting essentially of:
    (a) a pharmaceutically effective amount of a herbal medication as the active medication;
    (b) a polymeric matrix material;
    (c) a release enhancer;
    (d) a filler; and
    (e) a flavoring agent.

26. A method of releasing a medication in an oral cavity of a subject, comprising the steps of:
    (a) placing a tablet in the oral cavity of the subject, the tablet consisting essentially of:
       (i) a pharmaceutically effective amount of a herbal medication as the active medication;
       (ii) a polymeric matrix material;
       (iii) a release enhancer; and
       (iv) a filler; and
    (b) allowing said tablet to dissolve in the oral cavity of the subject, such that the medication is released.

* * * * *